(12) United States Patent
Itafuji et al.

(10) Patent No.: US 8,544,350 B2
(45) Date of Patent: Oct. 1, 2013

(54) SAMPLE INJECTOR

(75) Inventors: Hiroshi Itafuji, Komaki (JP); Masayuki Kouketsu, Komaki (JP)

(73) Assignee: CKD Corporation, Komaki-shi, Aichi (JP)

( * ) Notice: Subject to any disclaimer, the term of this patent is extended or adjusted under 35 U.S.C. 154(b) by 299 days.

(21) Appl. No.: 13/041,283

(22) Filed: Mar. 4, 2011

(65) Prior Publication Data

US 2011/0219890 A1 Sep. 15, 2011

(30) Foreign Application Priority Data

Mar. 10, 2010 (JP) ................................ 2010-053323

(51) Int. Cl.
*G01N 35/10* (2006.01)
*G01N 30/20* (2006.01)

(52) U.S. Cl.
CPC ............ *G01N 30/20* (2013.01); *G01N 35/1097* (2013.01)
USPC ... 73/864.83; 73/61.52; 73/61.56; 73/863.73; 73/864.81

(58) Field of Classification Search
USPC ................... 73/864.21, 61.56, 863.73, 864.83
See application file for complete search history.

(56) References Cited

U.S. PATENT DOCUMENTS

| | | | | |
|---|---|---|---|---|
| 3,230,048 A | * | 1/1966 | Skeggs | 422/70 |
| 3,908,463 A | * | 9/1975 | Bedo et al. | 73/863.73 |
| 4,068,528 A | * | 1/1978 | Gundelfinger | 73/864.84 |
| 4,577,515 A | * | 3/1986 | Someya et al. | 73/863.73 |
| 5,384,095 A | * | 1/1995 | Golz et al. | 422/501 |
| 5,419,208 A | * | 5/1995 | Schick | 73/863.73 |
| 5,616,300 A | * | 4/1997 | Ford et al. | 422/540 |
| 6,365,105 B1 | * | 4/2002 | Waters et al. | 422/70 |
| 6,623,630 B1 | * | 9/2003 | Staffler | 210/87 |
| 7,823,468 B2 | * | 11/2010 | Davison | 73/863.73 |
| 2002/0158022 A1 | * | 10/2002 | Huang et al. | 210/656 |

FOREIGN PATENT DOCUMENTS

| | | | |
|---|---|---|---|
| JP | 4-25683 | | 1/1992 |
| JP | 06180307 A | * | 6/1994 |
| JP | 8-5621 | | 1/1996 |
| JP | 2003-185645 | | 7/2003 |
| JP | 2007-121164 | | 5/2007 |

* cited by examiner

*Primary Examiner* — Hezron E Williams
*Assistant Examiner* — Alexander Mercado
(74) *Attorney, Agent, or Firm* — Beyer Law Group LLP

(57) ABSTRACT

This invention provides a sample injector for injecting a fixed amount of a sample into a mobile phase medium and discharging the mobile phase medium with the sample. The sample injector includes a first member having a medium passage for supplying the mobile phase medium and a sample passage for supplying the sample and a second member having a discharge passage for discharging the mobile phase medium with the sample to an outside of the injector. The second member is provided in contact with the first member. The first member and the second member are configured to move to a sample charging position and a sample injection position. The sample charging position is for the sample chamber to connect with the sample passage. The sample injection position is for the sample chamber to connect with the medium passage and the discharge passage.

15 Claims, 22 Drawing Sheets

SAMPLE INJECTOR

CROSS-REFERENCE TO RELATED APPLICATIONS

This application claims priorities of Japanese Patent Application No. 2010-53323 filed on Mar. 10, 2010 which is hereby incorporated by reference.

BACKGROUND OF THE INVENTION

1. Field of the Invention

The present invention relates to a sample injector used to inject a sample during chromatography in which a liquid or a gas is used as the sample.

2. Description of the Related Art

A sample injector used in liquid chromatography may be typically constituted using a flow passage switch valve. The flow passage switch valve realizes injection of a sample solution into a mobile phase solvent by switching appropriately between a mobile phase solvent flow passage and a sample solution flow passage. More specifically, FIG. 1 shows a conventional example employing a well-known hexagonal switch valve 99. The hexagonal switch valve 99 includes six ports numbered from 1 to 6, and realizes two flow passage states for sample charging (also referred to as loading) and sample injection, respectively.

During sample charging, two ports having port numbers 2 and 3 are connected such that the mobile phase solvent flow passage is formed from a pump to a column for separating the sample. At this time, two ports having port numbers 1 and 6 are connected simultaneously, and therefore a sample solution flow passage is formed from a port having a port number 4 to the port (a drain) having the port number 6 via a sample loop 98. As a result, the sample solution is loaded into the sample loop 98 from the port having the port number 4 using a syringe (not shown) while surplus liquid is discharged from the sample loop 98. During injection, on the other hand, the two ports having the port numbers 1 and 2 are connected and the two ports having the port numbers 3 and 4 are connected. Thus, a flow passage through which the sample loaded into the sample loop 98 is caused to flow back by a discharge pressure from the pump and thereby injected into the column is formed.

In the related art, this flow passage switching operation is typically performed by bringing two flat surfaces including a plurality of through holes into contact with each other and switching communication states between the plurality of through holes in the respective flat surfaces by rotationally sliding the flat surfaces against each other (Japanese Patent Application Publication No. H4-25683, Japanese Patent Application Publication No. H8-5621, Japanese Patent Application Publication No. 2003-185645, and Japanese Patent Application Publication No. 2007-121164). Meanwhile, a sample solution amount is measured on the basis of the syringe for injecting the sample or the amount of discharged surplus liquid.

When the communication states among the plurality of through holes in the related art are switched by a sliding motion, however, a complicated high-precision and an elastic sealing member must be used to realize the sliding motion, and a device for measuring the amount of injected sample as described above is also required. Such a complicated mechanism has a large number of components and is therefore difficult to reassemble after cleaning. Moreover, the present inventor has discovered that adjustments required during reassembly are difficult, making it difficult to maintain an initial performance. The present inventor also discovered that when an elastic sealing member is used, problems are likely to arise in terms of increases in the number of components, infiltration of foreign matter, and reduced wear life.

SUMMARY OF THE INVENTION

Accordingly, an object of the present invention is to solve at least a part of the conventional problems described above with a technique for simplifying the constitution of a sample injector for injecting a sample solution.

The above and other object of the present invention are attained at least partly by a sample injector for injecting a fixed amount of a sample into a mobile phase medium and discharging the mobile phase medium with the sample.

The sample injector includes a first member having a medium passage for supplying the mobile phase medium and a sample passage for supplying the sample, and a second member having a discharge passage for discharging the mobile phase medium with the sample to an outside of the injector. The second member is provided in contact with the first member. The first member and the second member have respective arc-shaped outer peripheral surfaces capable of a relative sliding motion with the surfaces keeping a contact. The medium passage and the sample passage of the first member and the discharge passage of the second member have openings onto the outer peripheral surfaces of the respective members. A sample chamber for charging the sample is formed in a recessed shape in the surface of either one of the first member and the second member. At least one of the first member and the second member is configured to move to a sample charging position and a sample injection position. The sample charging position is for the sample chamber to connect with the sample passage whereby the sample is charged into the sample chamber through the sample passage. The sample injection position is for the sample chamber to connect with the medium passage and the discharge passage whereby the sample is injected into the mobile phase medium flowing through the medium passage.

In the sample injector according to the first aspect, at least one of the first member and the second member is capable of moving relatively to the sample charging position and the sample injection position. In the sample charging position, the sample chamber connects with the sample passage such that the sample is charged into the sample chamber through the sample passage. The sample chamber is a formed in a recessed shape in the outer peripheral surface of one of the first member and the second member such that the sample flows therein. In the sample injection position, on the other hand, the sample chamber connects with the medium passage and the discharge passage such that the sample in the sample chamber is injected into the mobile phase medium.

According to the constitution described above, the sample can be charged into the sample chamber in the sample charging position, and the charged sample can be injected into the mobile phase medium in the sample injection position. Thus, the fixed amount of the sample can be injected into the mobile phase medium and then discharged to a downstream side together with the mobile phase medium.

These and other object, features, aspects and advantages of the present invention will become more apparent from the following detailed description of the preferred embodiments with the accompanying drawings.

DESCRIPTION OF THE PREFERRED EMBODIMENT

A specific embodiment of the present invention will be described below with reference to the drawings. In this embodiment, a high-speed chromatography apparatus for realizing high-speed liquid chromatography will be described.

Figure 1:
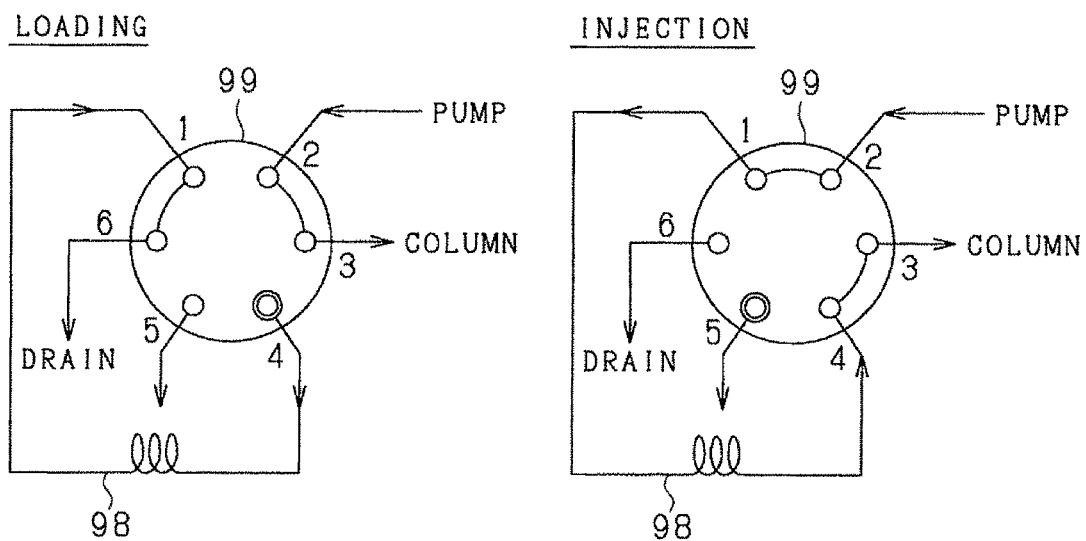
FIG. 1 is a pattern diagram showing a flow passage switch valve according to the related art.
Figure 2:
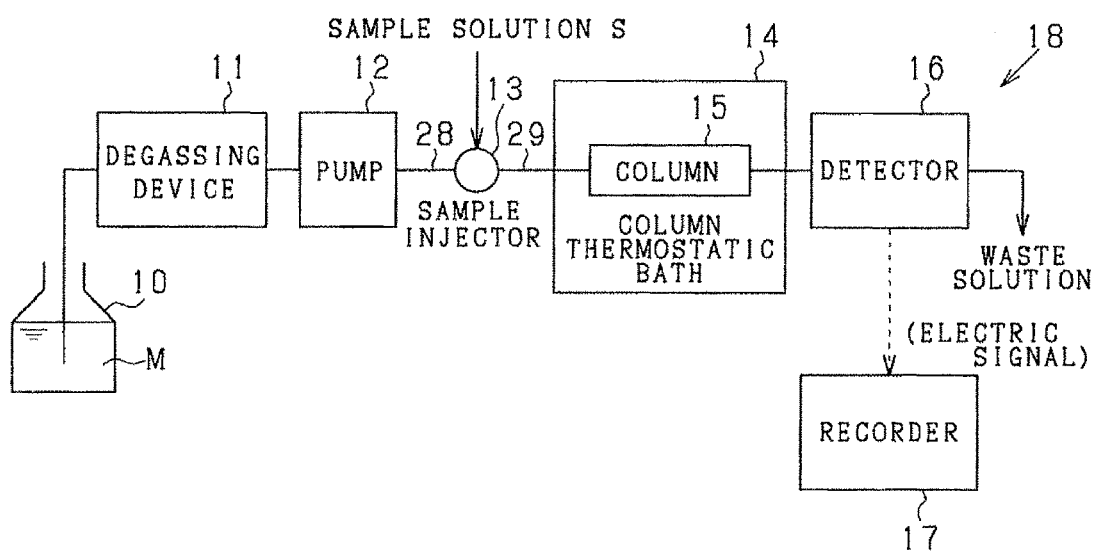
FIG. 2 is a pattern diagram showing the constitution of a high-speed chromatography apparatus according to an embodiment.

A. Constitution of High-Speed Chromatography Apparatus According to this Embodiment FIG. 2 is a pattern diagram showing the constitution of a high-speed chromatography apparatus 18 according to this embodiment. In high-speed liquid chromatography, a mobile phase solvent M is passed through a column 15 at a high flow velocity by applying high pressure thereto mechanically, and as a result, the time required for a sample serving as an analyte to accumulate in a stationary phase is shortened. Thus, increases in separation capacity and detection sensitivity are achieved. In high-speed chromatography, highly reproducible analysis can be performed comparatively easily by integrating processes from analyte sampling to detection and quantification, for example, such that these processes are performed automatically. High-speed chromatography is used frequently in analytic chemistry and biochemistry.

The high-speed chromatography apparatus 18 includes a solvent storage jar 10 for storing the mobile phase solvent M, a degassing device 11, a pump 12, a sample injector (to be referred to hereafter as an injector) 13, a column thermostatic bath 14, a column 15 disposed in the column thermostatic bath 14, a detector 16, and a recorder 17. The injector 13 is a sample injection device having a sample charging function and a flow passage switching function, which samples a sample solution S, or in other words charges the sample solution S into a sample chamber formed in the interior of the injector, and then injects the charged sample solution S into the mobile phase solvent M by switching an injector interior flow passage. By employing a liquid as a mobile phase medium and charging a stationary phase into a column, the high-speed chromatography apparatus 18 performs liquid column chromatography at high speed, enabling analysis of a minute amount of a sample.

The respective constitutional elements of the high-speed chromatography apparatus 18 have the following functions. The solvent storage jar 10 stores the mobile phase solvent M, and the degassing device 11 removes gases such as air bubbles and dissolved oxygen from the mobile phase solvent M supplied from the solvent storage jar 10. The pump 12 pressurizes the mobile phase solvent M to a predetermined high-pressure state and supplies the mobile phase solvent M in this high-pressure state to the injector 13 through a solvent pipe 28. The injector 13 injects the sample solution S serving as an analysis subject into the mobile phase solvent M and supplies the sample solution S together with the mobile phase solvent M to the column 15 through a solvent pipe 29 at high pressure.

In the column 15, a filler (not shown) functioning as the stationary phase is provided in a tubular vessel (not shown), a reaction mixture dissolved in a solvent is passed through the filler, and compounds are separated using differences thereof in affinity with the filler and molecule size. The column 15 is maintained at a predetermined temperature in the column thermostatic bath 14. The detector 16 detects each separated substance as an electric signal and transmits detection results to the recorder 17 in the form of electric signals. The solution that passes through the detector 16 is purified and then discarded. The recorder 17 records the electric signals as time series data, and calculates ingredient amounts and so on of the respective substances separated by the column 15 on the basis of peak values of the time series data, for example. The substances are converted into electric signals using optical properties (absorbance, refractive index, fluorescence, and so on), electrochemical properties, mass spectrometry, and so on.

Various types of solvents may be used as the mobile phase solvent M as long as the high-speed chromatography apparatus 18 (in particular the column 15) is not adversely affected thereby. More specifically, for example, water or a saline aqueous solution, alcohol, acetonitrile, dichloromethane, trifluoroacetate, and so on may be used. A mixture of compatible (intermixed) solvents is often used. The time required for analysis when a single sample is supplied to the column 15 varies greatly according to the substance to be analyzed and analysis parameters, but a single analysis typically takes between approximately several minutes and several tens of minutes.

Isocratic analysis and gradient analysis exist as types of analysis used in high-speed chromatography. Gradient analysis is a method of performing elution by continuously varying the composition of the solvent. More specifically, when a water/methanol gradient is used in reverse phase chromatography, for example, first a highly polar substance is eluted under a small amount of methanol, whereupon substances having steadily lower polarities are eluted in succession while gradually increasing the proportion of methanol.

Gradient analysis is advantaged in having a high degree of separation freedom, but a conditioning period is required during continuous analysis, and therefore the apparatus constitution is complicated. Isocratic analysis, meanwhile, is a method of performing elution without modifying the composition of the solvent. Although the degree of separation freedom is low, isocratic analysis is suited to continuous analysis. Moreover, the apparatus constitution can be simplified and stable analysis results can be obtained.

Figure 3:
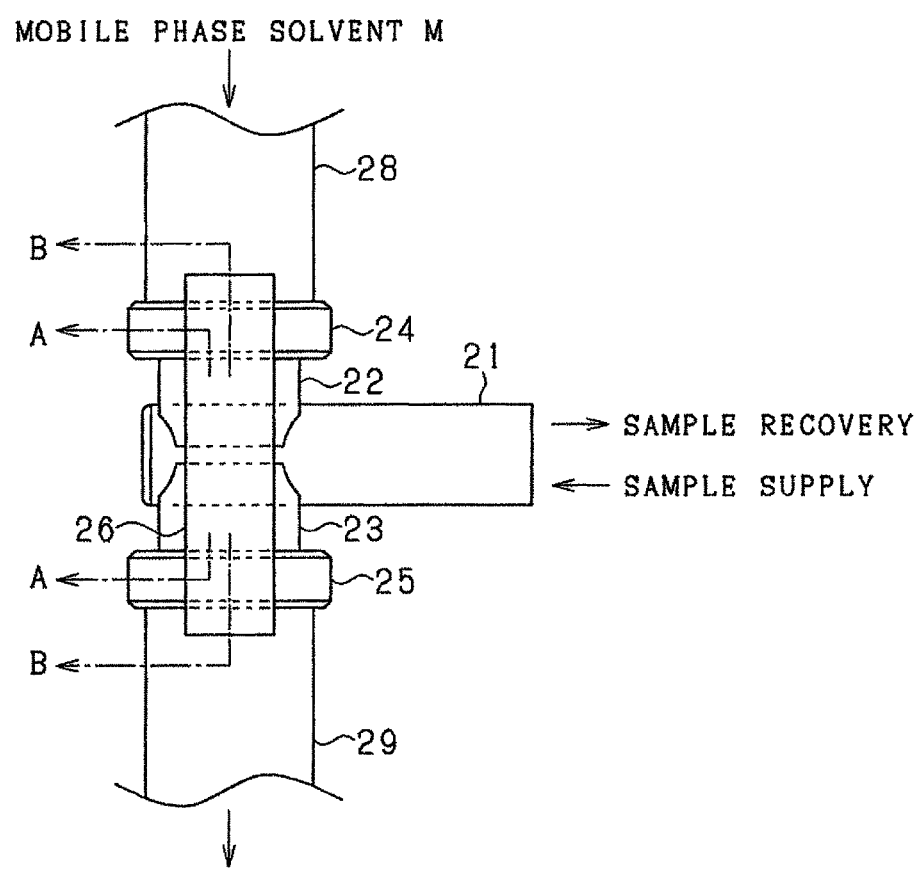
FIG. 3 is an external view showing the exterior of an injector.

Next, a basic constitution of the injector 13 will be described. FIG. 3 is a schematic diagram showing a constitution of the injector 13 when connected to the solvent pipes 28, 29. The injector 13 is a mechanical component for injecting the sample solution S into the mobile phase solvent M supplied through the solvent pipe 28 and discharging the sample solution S together with the mobile phase solvent M into the solvent pipe 29.

The injector 13 includes a columnar rotary body 21 for supplying and collecting the sample solution S, and a pair of support members 22, 23 provided to sandwich the rotary body 21. The rotary body 21 is held by the pair of support members 22, 23 to be capable of rotating about a central axis A thereof and incapable of displacing in an axial direction. As well as supporting the rotary body 21 to be capable of rotating, the support members 22, 23 function to supply the mobile phase solvent M to the rotary body 21 side (take the mobile phase solvent M into the injector) and discharge the mobile phase solvent M and the sample solution S to an injector downstream side. Note that for ease of description, the support member 22 and the support member 23 will also be referred to as a first support member 22 and a second support member 23, respectively. In this embodiment, the rotary body 21 corresponds to a "first member" and the second support member 23 corresponds to a "second member".

The first support member 22 is connected to the solvent pipe 28 via a joint member 24, and the second support member 23 is connected to the solvent pipe 29 via a joint member 25. Further, a fixing member 26 for causing the support members 22, 23 to contact an outer peripheral surface of the rotary body 21 tightly and maintaining this state is provided on the joint members 24, 25 provided to sandwich the injector 13. The fixing member 26 may be constituted as desired as long as it is capable of keeping the support members 22, 23 in close contact with the rotary body 21, but preferably has a fastening function realized by a screw or the like so that the support members 22, 23 can be pressed against the rotary body 21. The number of disposed fixing members 26 is arbitrary. The fixing member 26 may apply a pressing force to the support members 22, 23 directly rather than via the joint members 24, 25.

The rotary body 21, when rotated relative to the support members 22, 23, functions as a flow passage switch valve for switching between a flow passage for the sample solution S and a flow passage for the mobile phase solvent M. In other words, the injector 13 can inject the sample solution S by switching the flow passage using the rotary body 21.

Figure 4:
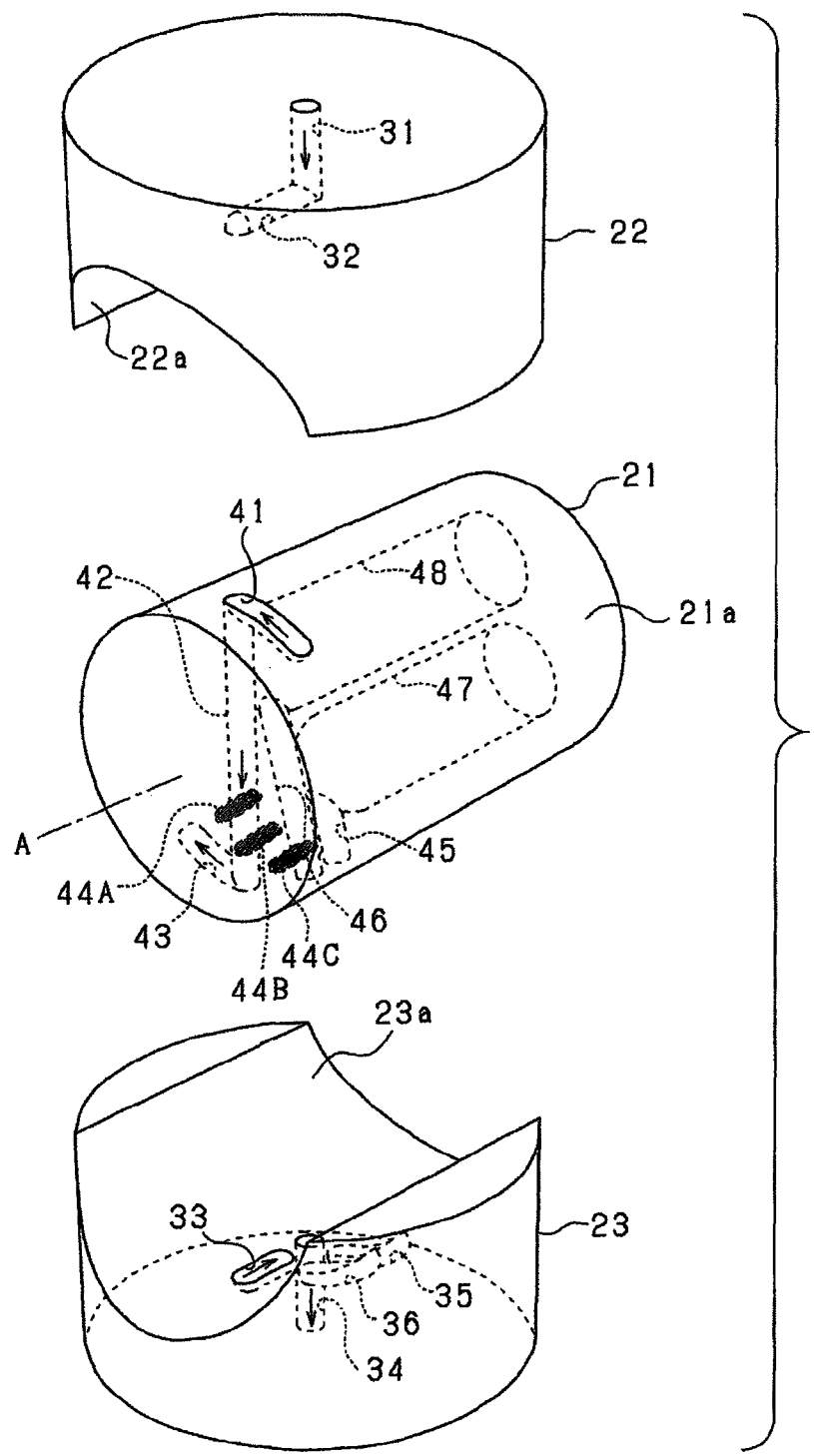
FIG. 4 is an exploded perspective view showing main constitutional elements of the injector in exploded form.
Figure 5A:
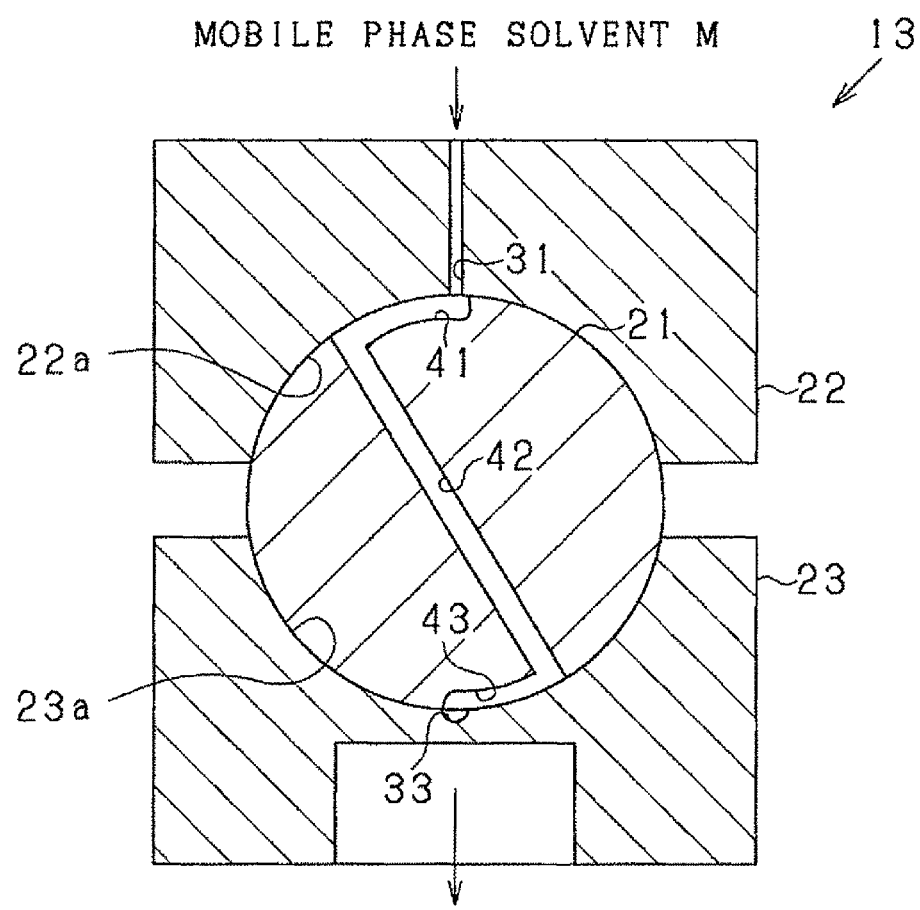
FIG. 5A is a sectional view showing an A-A line cross-section of an injector main portion of FIG. 3.
Figure 5B:
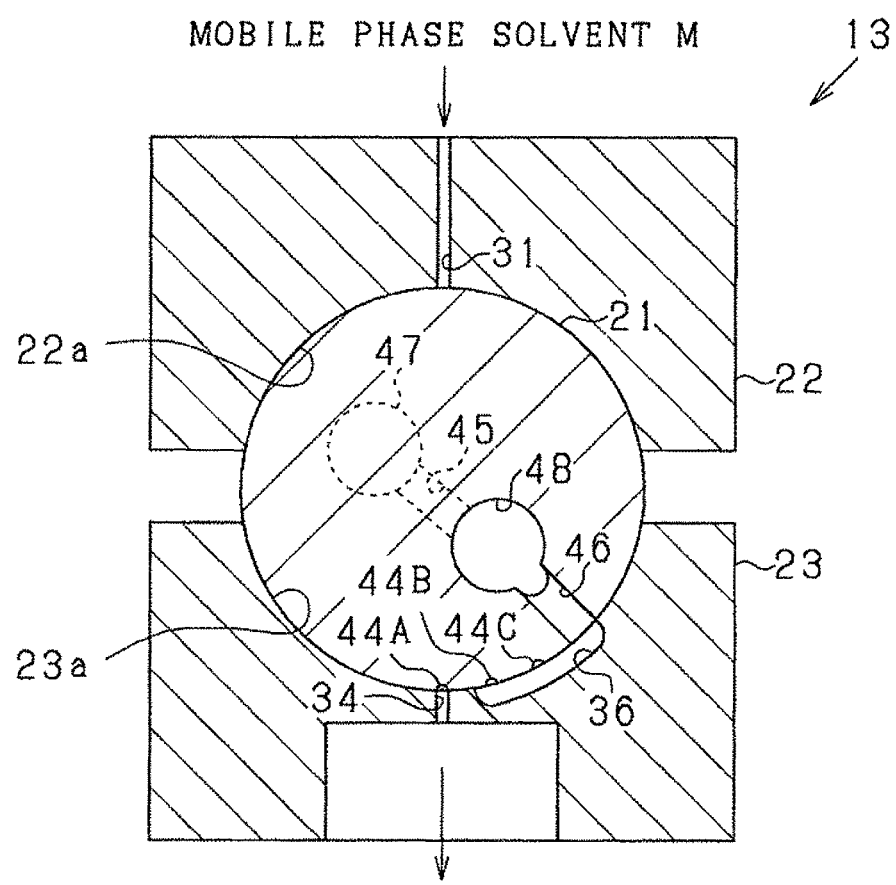
FIG. 5B is a sectional view showing an B-B line cross-section of an injector main portion of FIG. 3.

Next, constitutions relating to the flow passage switching operation performed by the injector 13 will be described in detail. FIG. 4 is an exploded perspective view showing the main constitutional elements of the injector 13 in exploded form. Further, FIGS. 5A, 5B are sectional views showing a cross-section of an injector main portion. FIG. 5A is an A-A line sectional view of FIG. 3, and FIG. 5B is a B-B line sectional view of FIG. 3.

Figure 6:
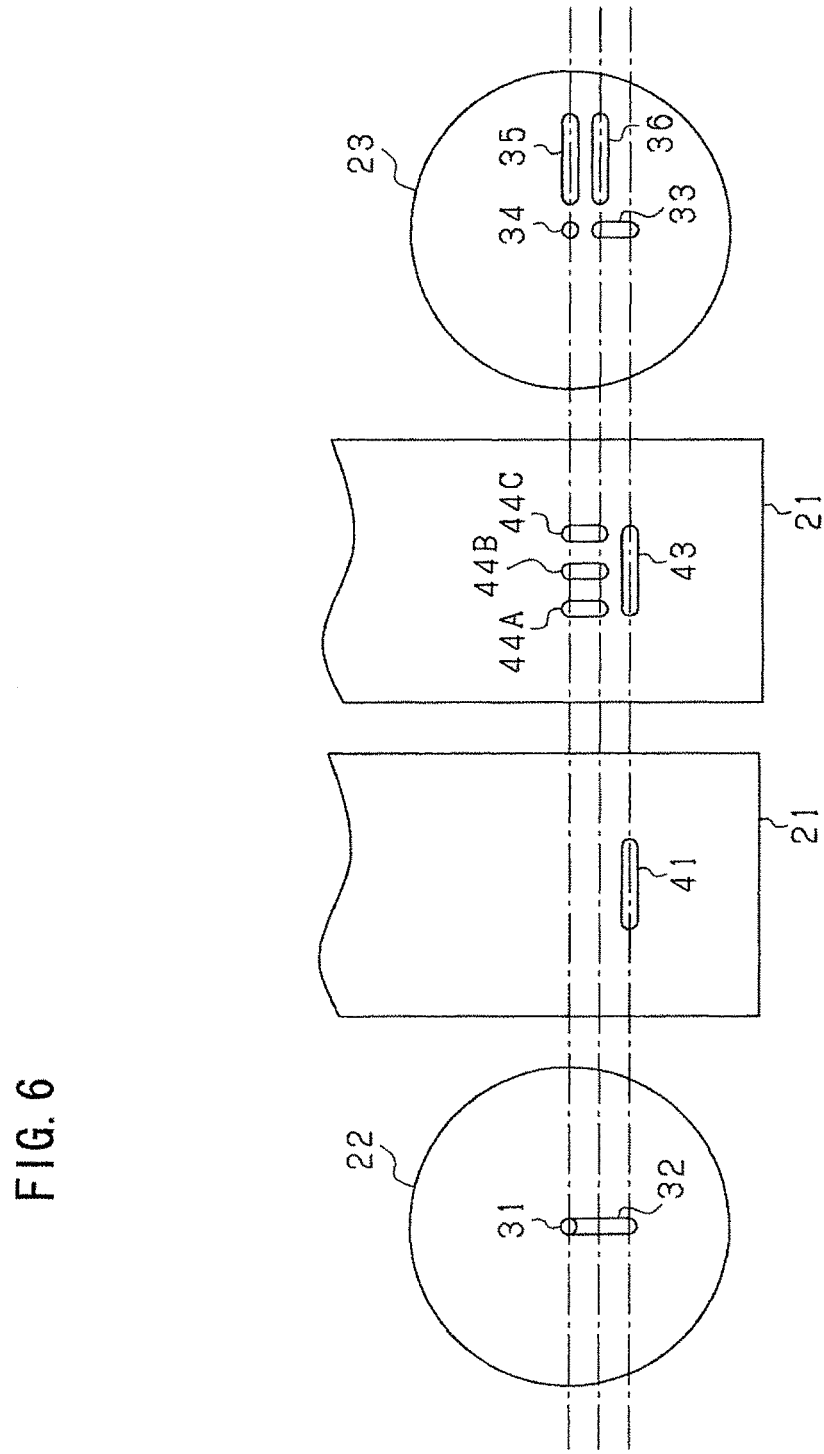
FIG. 6 is a sectional view showing broadly divided flow passage configurations of the illustrated injector.

Note that FIGS. 5A, 5B show only the rotary body 21 and the support members 22, 23. Furthermore, FIG. 6 is a view illustrating arrangements and positional relationships of passages provided in the rotary body 21 and the support members 22, 23. FIG. 6 shows, in pattern form, a contact surface of the first support member 22, a contact surface of the rotary body 21 on the first support member 22 side, a contact surface of the rotary body 21 on the second support member 23 side, and a contact surface of the second support member 23.

As shown in FIGS. 4, 5A and 5B, the two support members 22, 23 are substantially columnar components attached to the rotary body 21 such that respective axes thereof are orthogonal to the axis (the central axis A) of the rotary body 21. In this case, arc-shaped recess portions 22a, 23a are formed respectively in sites of the support members 22, 23 that contact the rotary boy 21, and outer peripheral surfaces of the recess portions 22a, 23a are arc-shaped surfaces formed in a recessed arc shape to correspond to the outer shape of the rotary body 21. In other words, the rotary body 21 and the support members 22, 23 are capable of performing a relative sliding motion while maintaining surface contact on the respective arc-shaped outer peripheral surfaces thereof. A radius of the arc of the recess portions 22a, 23a (arc-shaped surfaces) is set to be smaller than an outer diameter radius of the rotary body 21. Note, however, that the radius of the arc of the recess portions 22a, 23a may take an identical dimension to the outer diameter radius of the rotary body 21, or the magnitude relationship therebetween may be reversed.

A depth dimension of the recess portions 22a, 23a is set to be smaller than the radius of the rotary body 21, and therefore a gap is formed between the two support members 22, 23. The outer peripheral surface of the rotary body 21 and recess portion surfaces of the respective support members 22, 23 form sliding surfaces when the rotary body 21 rotates relative to the support members 22, 23. Note that in this embodiment, a radius of the respective support members 22, 23 (a radius of the columnar part) is set to be larger than the radius of the rotary body 21, but the respective radii may be equal, or the magnitude relationship therebetween may be reversed. Further, the outer shape of the support members 22, 23 is arbitrary and may be a prism shape. Moreover, the support members 22, 23 may have different sizes and outer shapes.

In the first support member 22, an inflow side passage 31 for supplying the mobile phase solvent M that flows in through the solvent pipe 28 to the rotary body 21 side is formed in a central portion of the recess portion 22a, or in other words a most recessed part of the recess portion 22a (also referred to as an apex portion of the recess portion). Further, a groove portion 32 that extends in the axial direction of the rotary body 21 from an outlet side end portion of the inflow side passage 31 is formed in the recess portion 22a. Note that for convenience, FIGS. 5A and 5B show the inflow side passage 31 using solid lines, but in actuality, the inflow side passage 31 exists further back than a cross-section position of these drawings.

In the second support member 23, an outflow side passage 34 for discharging the mobile phase solvent M and so on to the solvent pipe 29 is formed in a central portion of the recess portion 23a, or in other words a most recessed part of the recess portion 23a. Further, in the recess portion 23a, a groove portion 33 extending in the axial direction of the rotary body 21 is formed in a positioned removed from an inlet side end portion of the outflow side passage 34 in the axial direction, and two groove portions 35, 36 extending parallel to each other in a circumferential direction of a recess portion inner peripheral surface are formed in positions removed from the outflow side passage 34 and the groove portion 33 in the circumferential direction.

Meanwhile, as shown in FIGS. 4 and 5A, a solvent passage 42 is formed in the rotary body 21 so as to traverse the central portion of the rotary body 21. Further, groove portions 41, 43 extending in a circumferential direction of the rotary body 21 are formed in the outer peripheral surface of the rotary body 21 on a first support member 22 side end portion and a second support member 23 side end portion of the solvent passage 42, respectively. The solvent passage 42 serves to discharge the mobile phase solvent M that flows in through the inflow side passage 31 and the groove portion 32 of the first support member 22 to the groove portion 33 of the second support member 23. In this case, the groove portions 41, 43 extending in the circumferential direction of the rotary body are provided on the two end portions of the solvent passage 42, and therefore communication is maintained between the solvent passage 42 and the inflow side passage 31 and between the solvent passage 42 and the groove portion 33 even when the rotary body 21 rotates within a predetermined rotary angle range.

Note that a groove length (a length in the rotary body circumference direction) of the groove portion 43 is substantially identical to a groove length (a length in the rotary body circumference direction) of the groove portions 35, 36 formed in the second support member 23. Further, a groove length (a length in the rotary body axis direction) of the groove portion 33 formed in the second support member 23 is at least equal to a separation distance between the groove portion 36 on the second support member 23 side and the groove portion 43 on the rotary body 21 side.

Further, as shown in FIGS. 4 and 5B, an intake passage 48 for taking in the sample solution S supplied from the outside (a syringe or the like) and a collecting passage 47 for collecting surplus sample solution S from the injector 13 are formed in the rotary body 21 to extend in the axial direction of the rotary body 21. Furthermore, a sample inflow passage 46 connecting one end portion of the intake passage 48 to the outer peripheral surface of the rotary body 21 is formed in the intake passage 48, and a sample outflow passage 45 connecting one end portion of the collecting passage 47 to the outer peripheral surface of the rotary body 21 is formed in the collecting passage 47. The sample inflow passage 46 and the sample outflow passage 45 are provided in series in the axial direction of the rotary body 21 such that outer peripheral side end portions thereof connect respectively with the groove portions 35, 36 formed in the second support member 23. In this case, the groove portions 35, 36 are provided to extend in the circumferential direction of the recess portion inner peripheral surface, and therefore communication is maintained between the sample inflow passage 46 and the groove portion 36 and between the sample outflow passage 45 and the groove portion 35 even when the rotary body 21 rotates within a predetermined rotary angle range.

Moreover, groove-shaped (recessed) recess portion chambers 44A, 44B, 44C extending parallel to each other in the axial direction of the rotary body 21 are formed in the outer peripheral surface of the rotary body 21. Note that in FIG. 4, the recess portion chambers 44A to 44C are shaded to facilitate comprehension. The recess portion chambers 44A to 44C form spaces having predetermined volumes relative to the recess portion surface of the second support member 23. The respective recess portion chambers 44A to 44C may have identical volumes or include at least two different volumes. In this embodiment, the respective volumes of the recess portion chambers 44A to 44C are assumed to be identical. Further, the recess portion chambers 44A to 44C are respectively formed at a length enabling them to straddle the outflow side passage 34 and the groove portion 33 and straddle the two groove portions 35, 36 (the lengths of the grooves are identical). The recess portion chambers 44A to 44C are formed to extend in a direction that intersects the groove portions 35, 36 formed in the second support member 23 (an orthogonal direction in this embodiment).

In the rotary body 21, the three recess portion chambers 44A to 44C are disposed at intervals respectively corresponding to the length of the groove portion 43 (downstream side groove portion) connected to the solvent passage 42. The recess portion chamber 44A, the recess portion chamber 44B, and the recess portion chamber 44C are provided to the side (to the side in the axial direction; likewise hereafter) of one side end portion of the groove portion 43, to the side of a central portion of the groove portion 43, and to the side of another side end portion of the groove portion 43, respectively.

When the rotary body 21 rotates, the recess portion chamber 44 (any of 44A to 44C) enters one of the following states in accordance with the rotation.

(1) The recess portion chamber 44 straddles the outflow side passage 34 and the groove portion 33.

(2) The recess portion chamber 44 straddles the two groove portions 35 and 36.

(3) The recess portion chamber 44 straddles neither the outflow side passage 34 and groove portion 33 nor the groove portions 35 and 36.

In the state described in (1), the mobile phase solvent M (high-pressure solvent) flows in order of the solvent passage 42→the groove portion 43→the groove portion 33→the recess portion chamber 44→the outflow side passage 34. In the state described in (2), the sample solution S flows in order of the sample inflow passage 46→the groove portion 36→the recess portion chamber 44→the groove portion 35→the sample outflow passage 45. In the state described in (2), the sample solution S is charged to the recess portion chamber 44, and at this time, inflow and outflow (collection) of the sample solution S to and from the recess portion chamber 44 occurs continuously. Therefore, even when air bubbles, foreign matter, and so on exist in the recess portion chamber 44, the air bubbles, foreign matter, and so on can be carried on the flow of the sample solution S and thereby discharged to the outside. In the state described in (3), inflow/outflow of the mobile phase solvent M and the sample solution S relative to the recess portion chamber 44 does not occur. When, in the case of (3), the sample solution S is already charged into the recess portion chamber 44, the sample charged state is maintained.

With the constitution of this embodiment, when the recess portion chamber 44A, for example, of the three recess portion chambers 44A to 44C, is in the state described above in (1), the other recess portion chambers 44B, 44C can be set in the state described in (2) simultaneously. In other words, when the sample solution S is charged to the recess portion chambers 44B, 44C, a charging path can be made independent of the flow path for the mobile phase solvent M, thereby ensuring that the mobile phase solvent M does not become mixed into the recess portion chambers 44B, 44C while sample charging is underway. Hence, by providing this two-system flow path, the mobile phase solvent M can be introduced into one recess portion chamber 44 (the recess portion chamber 44A, for example) at the same time as the sample solution S is introduced into another recess portion chamber 44 (the recess portion chambers 44B, 44C, for example).

In this embodiment, a state in which the recess portion chamber 44A corresponds to the state described in (2) and the other recess portion chambers 44B, 44C correspond to the state described in (1) is set as an initial state, or in other words a preparatory state for sample injection into the mobile phase solvent M. When the rotary body 21 is rotated in a predetermined direction from the initial state, the sample solution S already charged into the recess portion chambers 44B, 44C is injected successively into the mobile phase solvent M.

The groove portions 35, 36 are shaped to extend in the circumferential direction of the rotary body 21, and therefore the sample solution S can be caused to flow into the two recess portion chambers 44B, 44C simultaneously.

Hence, the injector 13 is constituted such that during flow passage switching between the rotary body 21 and the support members 22, 23, the rotary body 21 and the support members 22, 23 are capable of performing a relative sliding motion while maintaining surface contact between the respective arc-shaped outer peripheral surfaces thereof. With this constitution, leakage from the contact surface can be managed appropriately, and therefore flow passage switching and sample injection amount measurement can be realized without the use of a high-precision rotary mechanism and an elastic sealing member. Accordingly, the injector 13 can be used favorably in a chromatography apparatus that supplies a mobile phase medium in a high-pressure state, for example.

Further, with the above constitution, in which a relative sliding motion can be performed while maintaining surface contact between the respective arc-shaped outer peripheral surfaces, a surface pressure distribution can be adjusted by differentiating a radius of the recessed arc-shaped outer peripheral surfaces 22a, 23a (also referred to as recessed arc-shaped surfaces) from a radius of the projecting arc-shaped outer peripheral surface 21a (also referred to as a projecting arc-shaped surface), and thus a degree of design freedom can be provided. As a result, a sealing performance with respect to communication among the respective flow passages can be set freely in accordance with design specifications of the sample injector. More specifically, constitutions such as the following, for example, can be implemented.

By setting the radius of the recessed arc-shaped surfaces 22a, 23a to be smaller than the radius of the projecting arc-shaped surface 21a, surface pressure can be generated over a large region of the contact surface when the respective arc-shaped surfaces are pressed into close contact with each other. Thus, a region in which a sufficient sealing performance is secured relative to specifications can be realized without the use of an elastic sealing member, for example, and as a result, the design freedom (the number of sample chambers, for example) of the flow passages can be increased.

Conversely, by setting the radius of the recessed arc-shaped surfaces 22a, 23a to be larger than the radius of the projecting arc-shaped surface 21a, a surface pressure distribution having a sharp peak in a most recessed part of the recessed arc-shaped surfaces 22a, 23a (also referred to as a linear region in an axial direction of an apex portion of the recessed portion) can be realized. The reason for this is that the respective arc-shaped surfaces are brought into close contact by large elastic deformation in the most recessed part of the recessed arc-shaped surfaces 22a, 23a. This constitution is favorable in a case where a pressure in the flow passage for charging the sample is low such that sealing performance requirements are low, whereas a pressure in the flow passage for injecting the sample into the mobile phase medium in the sample injection position is extremely high such that a high sealing performance is required locally, for example. Alternatively, a precise fitting tolerance may be set.

Hence, in this embodiment, a relative sliding motion can be performed while maintaining surface contact between the respective arc-shaped outer peripheral surfaces, and therefore a sealing performance with respect to communication among the respective flow passages can be set freely in accordance with the design specifications of the sample injector.

Note that at least one of the rotary body 21 and the support member 22 preferably includes indentations (not shown) for positioning the direction of the central axis A (rotary axis) of the rotary body 21 relative to the support members 22, 23. Thus, the axial directions of the respective members can be positioned easily.

Further, the rotary body 21 and the support members 22, 23 may be manufactured by subjecting a ceramic-based material, for example to laser microprocessing to form through holes such as the holes 31, 42, 34 and recess portion shapes such as the recess portions 32, 41, 33. Note, however, that the material and processing method are not limited thereto, and instead, a metallic material such as silicon carbide SiC or stainless steel may be processed using another usable processing method.

B. Operation of High-Speed Chromatography Apparatus

Next, the operation of the high-speed chromatography apparatus 18, centering on an operation of the injector 13, will be described. Here, flow passage configurations of the injector 13 are broadly divided into four states, which are shown in FIGS. 7A to 7D. Note that FIGS. 7A to 7D correspond (shows an identical cross-sectional position) to FIG. 5B, and FIGS. 7A to 7D show states achieved by rotating the rotary body 21 little by little in a clockwise direction of the drawing.

Figure 7A:
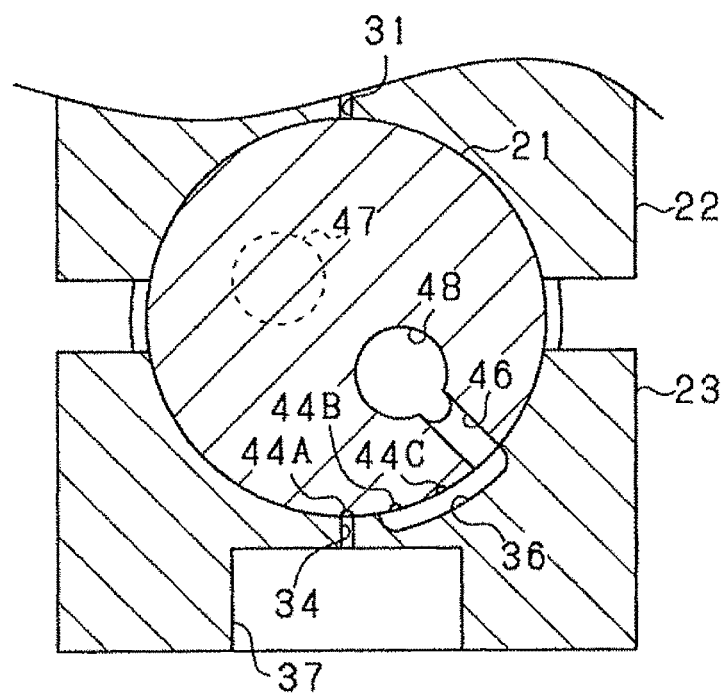
FIG. 7A is a sectional view showing broadly divided flow passage configurations of the injector.
Figure 7B:
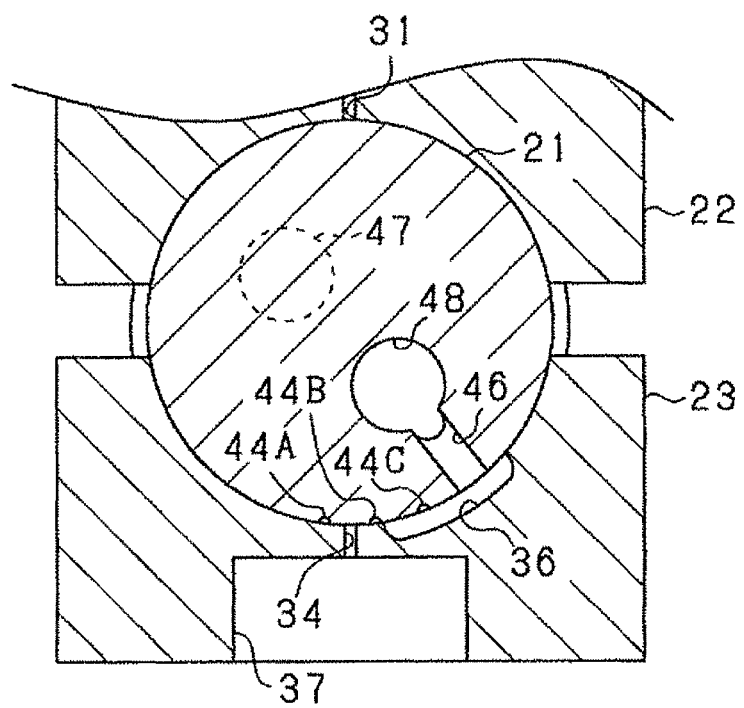
FIG. 7B is a sectional view showing broadly divided flow passage configurations of the injector.
Figure 7C:
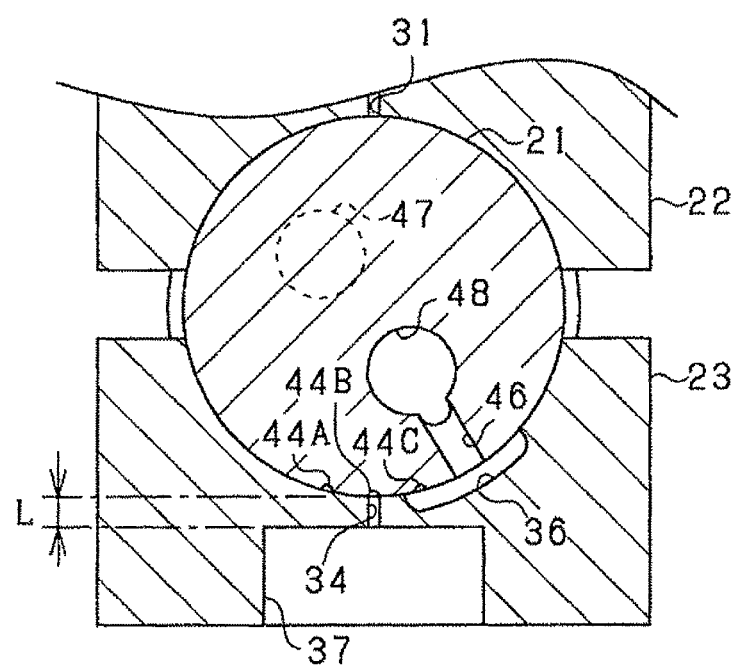
FIG. 7C is a sectional view showing broadly divided flow passage configurations of the injector.
Figure 7D:
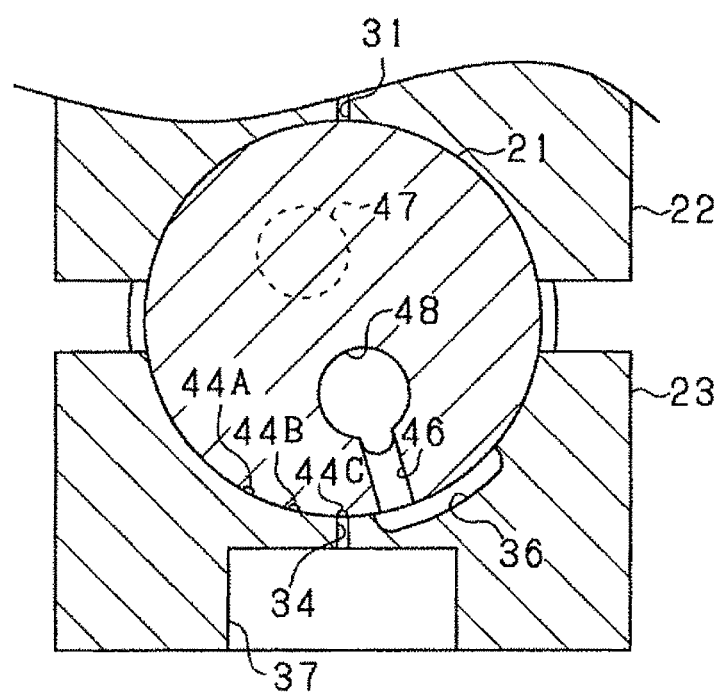
FIG. 7D is a sectional view showing broadly divided flow passage configurations of the injector.

FIG. 7A shows the initial state of the injector 13, in which the sample inflow passage 46 connects with one end side of the groove portion 36, and of the three recess portion chambers 44A to 44C, the recess portion chamber 44A is positioned to connect with the outflow side passage 34 while the other recess portion chambers 44B, 44C are positioned to connect with the groove portion 36. In FIGS. 7B to 7D, to be described below, the sample inflow passage 46 and the groove portion 36 remain in a communicative state even though communication positions thereof vary.

FIG. 7B shows a state in which the recess portion chambers 44A, 44B, of the three recess portion chambers 44A to 44C, are positioned to connect with neither the outflow side passage 34 nor the groove portion 36, and only the recess portion chamber 44C is positioned to connect with the groove portion 36. Note that from this state onward, the recess portion chamber 44A no longer connects with either the outflow side passage 34 or the groove portion 36.

FIG. 7C shows a state in which the recess portion chamber 44B, of the three recess portion chambers 44A to 44C, is positioned to connect with the outflow side passage 34 and only the recess portion chamber 44C is positioned to connect with the groove portion 36. FIG. 7D shows a state in which the recess portion chamber 44C, of the three recess portion chambers 44A to 44C, is positioned to connect with the outflow side passage 34.

In each of the states described above, the injector 13 is switched appropriately in accordance with the stage of the sample injection process. Actions performed prior to sample injection and during sample injection will be described in detail below.

Note that FIG. 7A shows a state in which the rotary body 21 "is in a medium outflow position of the recess portion chamber 44A and a sample charging position of the recess portion chambers 44B, 44C", FIG. 7C shows a state in which the rotary body 21 "is in a sample injection position of the recess portion chamber 44B and the sample charging position of the recess portion chamber 44C", and FIG. 7D shows a state in which the rotary body 21 "is in the sample injection position of the recess portion chamber 44C".

(B-1. Prior to Sample Injection)

Figure 8:
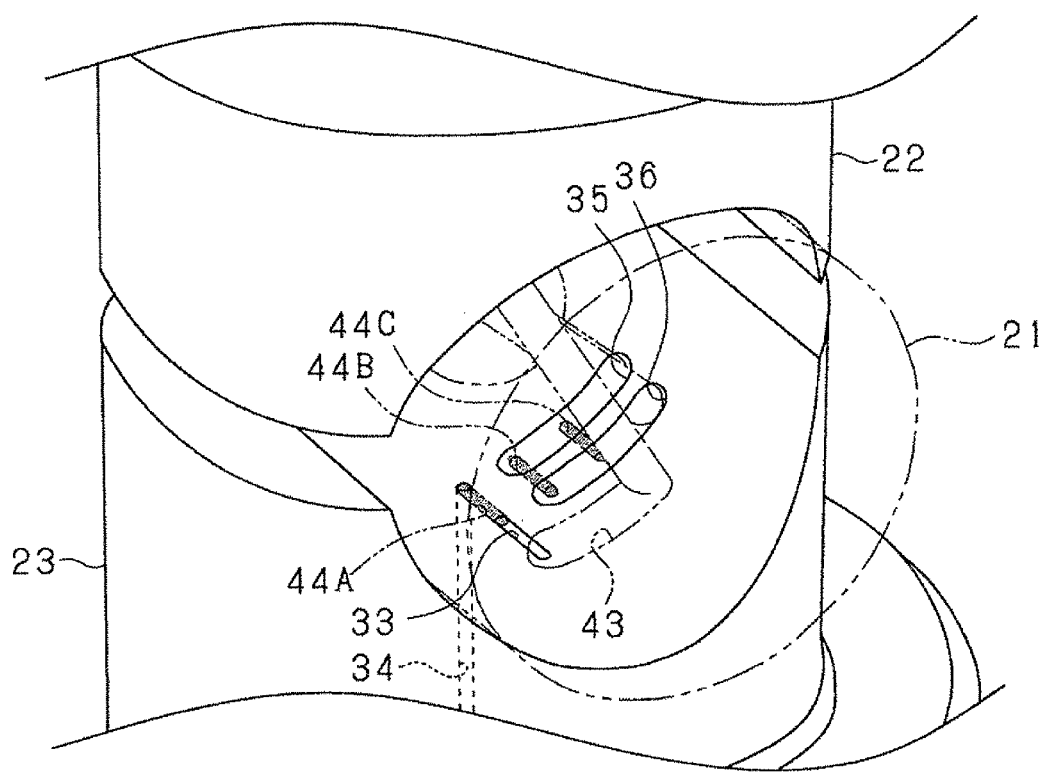
FIG. 8 is a perspective view illustrating a flow passage configuration of the injector prior to sample injection.
Figure 9A:
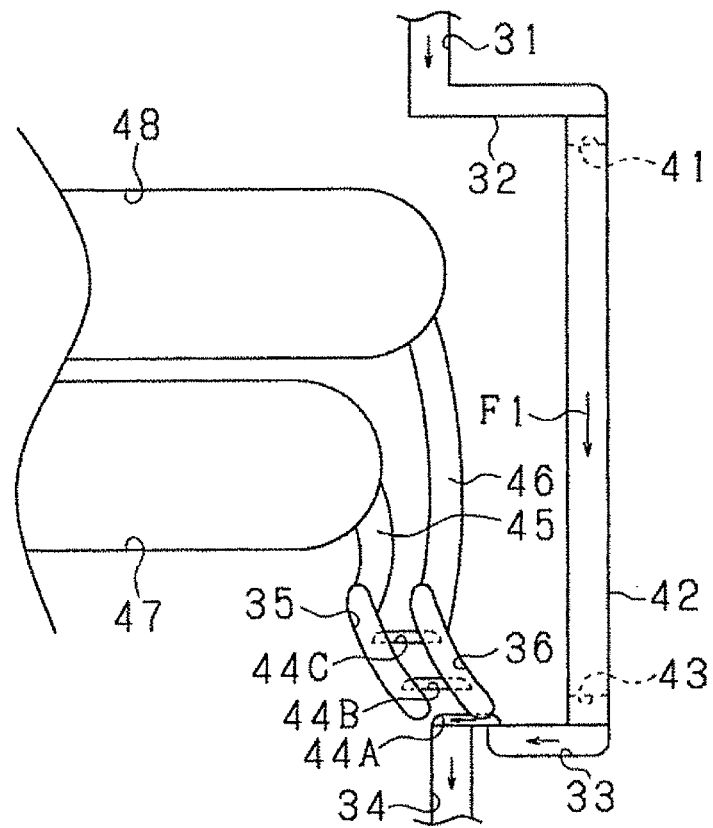
FIG. 9A is a pattern diagram illustrating the flow passage configuration of the injector prior to sample injection.
Figure 9B:
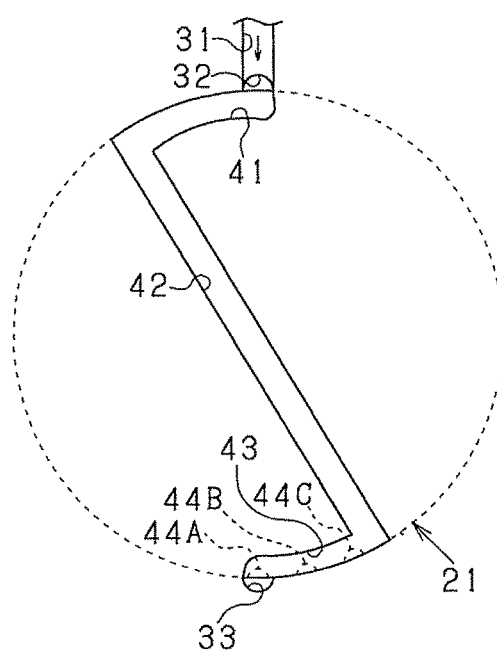
FIG. 9B is a pattern diagram illustrating the flow passage configuration of the injector prior to sample injection.

A flow passage configuration of the injector 13 prior to injection of the sample solution S will now be described using FIGS. 8, 9A, and 9B. FIG. 8 is a perspective view illustrating the flow passage configuration of the injector 13 prior to sample injection. FIGS. 9A and 9B are pattern diagrams illustrating the flow passage configuration of the injector 13 prior to sample injection. FIG. 9A is a pattern diagram seen from an orthogonal orientation to the rotary body axis direction, and FIG. 9B is a pattern diagram seen from the rotary body axis direction.

In the state prior to sample injection, i.e. the state shown in FIG. 7A, the mobile phase solvent M flows through the recess portion chamber 44A, of the three recess portion chambers 44A to 44C, and the sample solution S flows through the other recess portion chambers 44B, 44C. At this time, the mobile phase solvent M (high-pressure solvent) flows along a solvent flow path formed from the solvent passage 42→the groove portion 43→the groove portion 33→the recess portion chamber→44A the outflow side passage 34, in that order. In other words, the mobile phase solvent M alone is discharged from the injector 13 to the solvent pipe 29 and supplied to the downstream side column 15. In the column 15, conditioning (condition adjustment) is performed in the column interior by the mobile phase solvent M supplied from the injector 13. As a result, the condition in the column interior can be stabilized and advance preparation for a sample test can be performed.

The sample solution S flows in order of the sample inflow passage 46→the groove portion 36→the recess portion chambers 44B, 44C→the groove portion 35→the sample outflow passage 45. As a result, a predetermined amount of the sample solution S is charged to the two recess portion chamber 44B, 44C.

(B-2. During Sample Injection)

Figure 10:
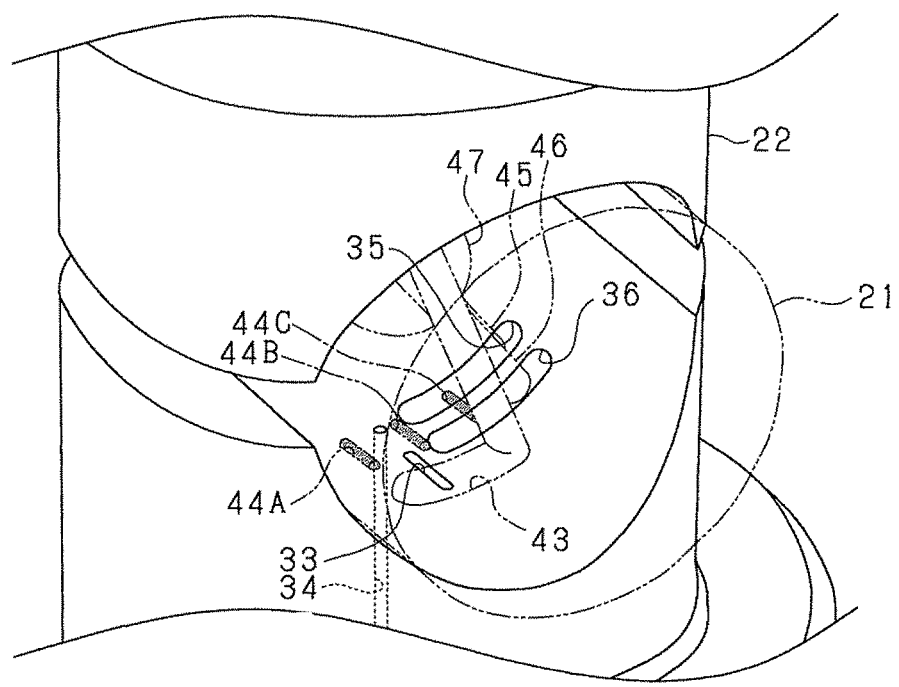
FIG. 10 is a perspective view illustrating a flow passage configuration of the injector during sample injection.
Figure 11:
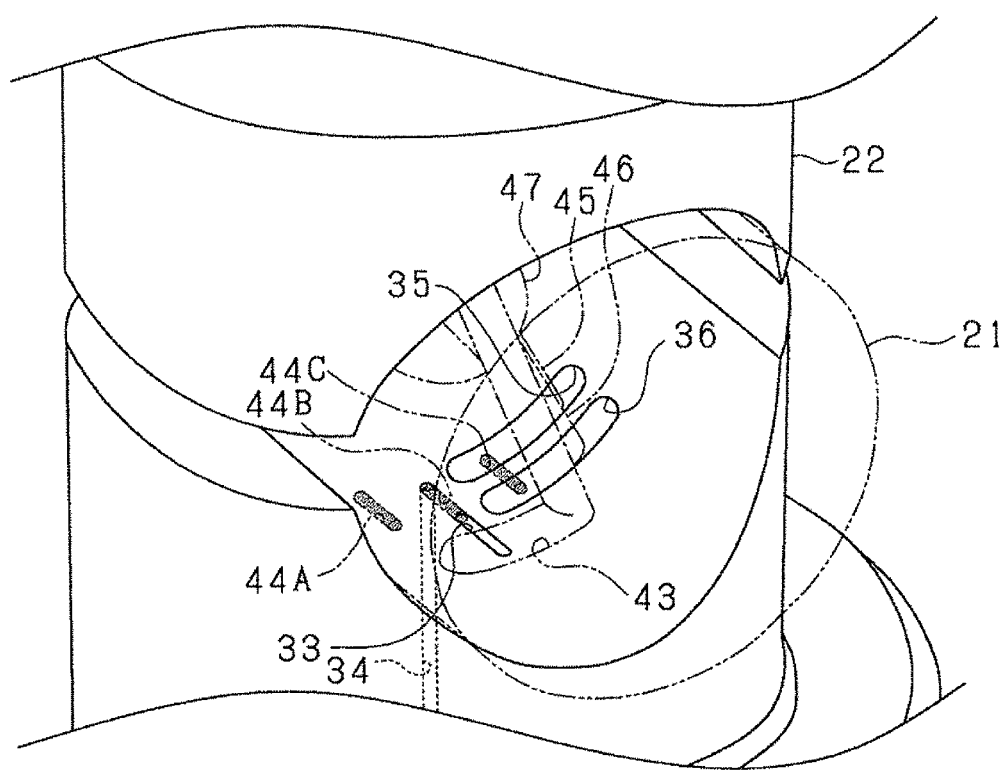
FIG. 11 is a perspective view illustrating the flow passage configuration of the injector during sample injection.
Figure 12A:
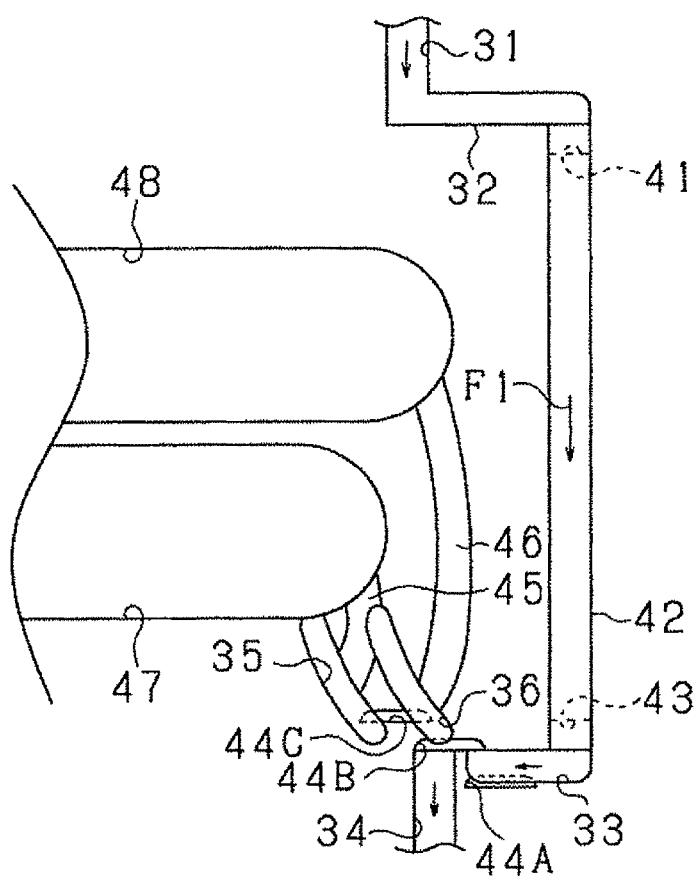
FIG. 12A is a pattern diagram illustrating the flow passage configuration of the injector during sample injection.
Figure 12B:
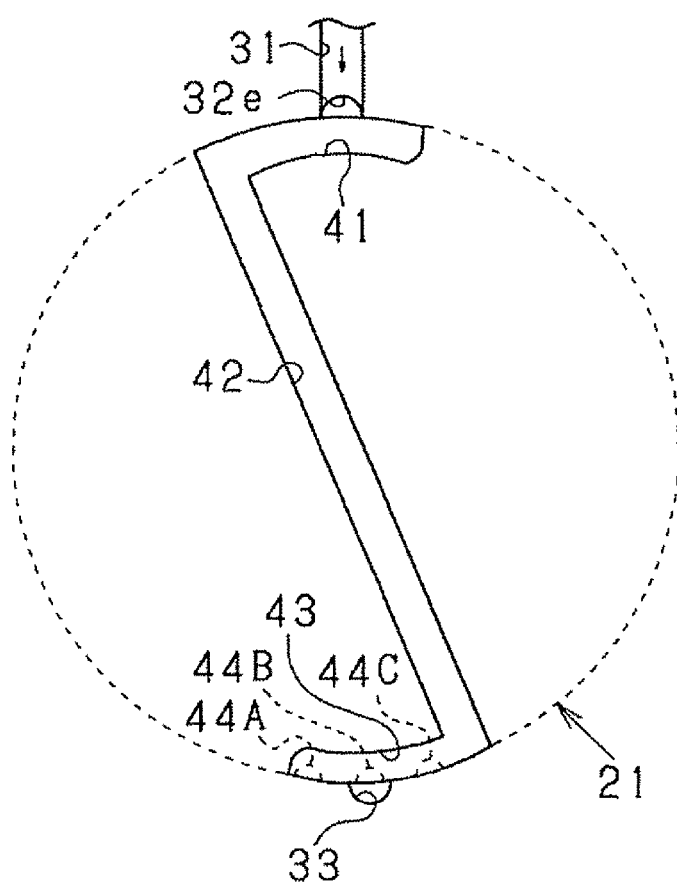
FIG. 12B is a pattern diagram illustrating the flow passage configuration of the injector during sample injection.
Figure 13:
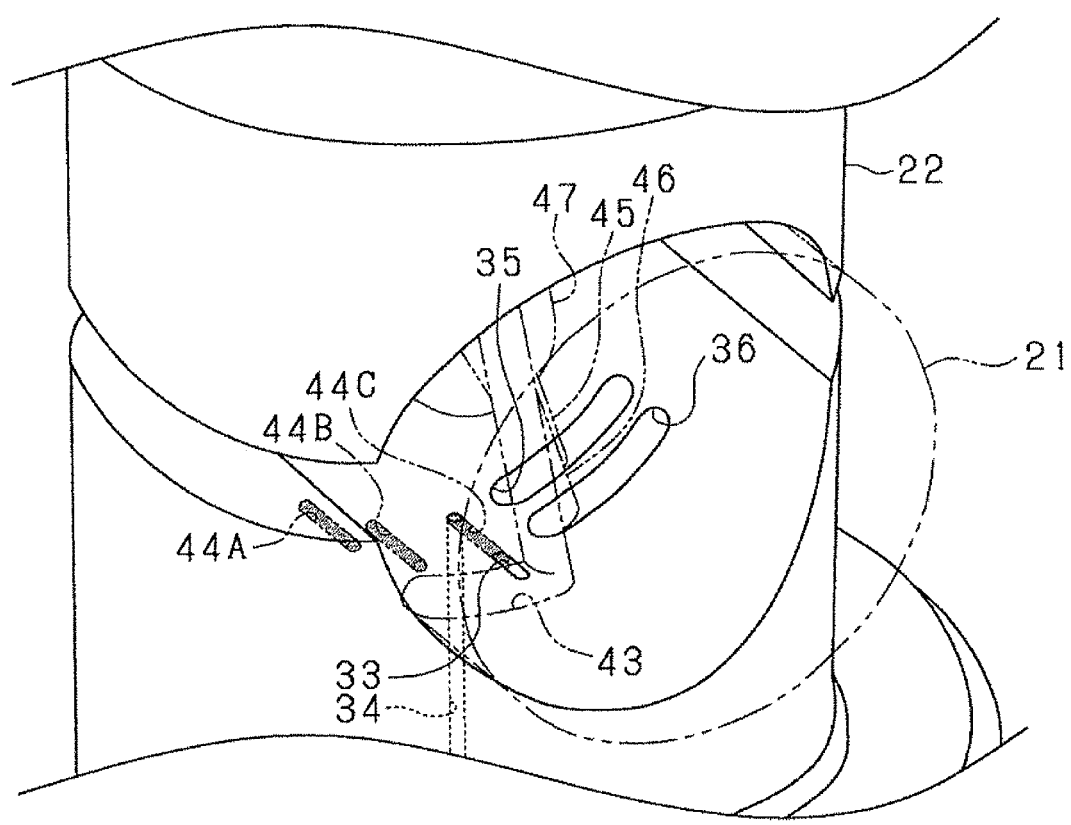
FIG. 13 is a perspective view illustrating the flow passage configuration of the injector during sample injection.
Figure 14A:
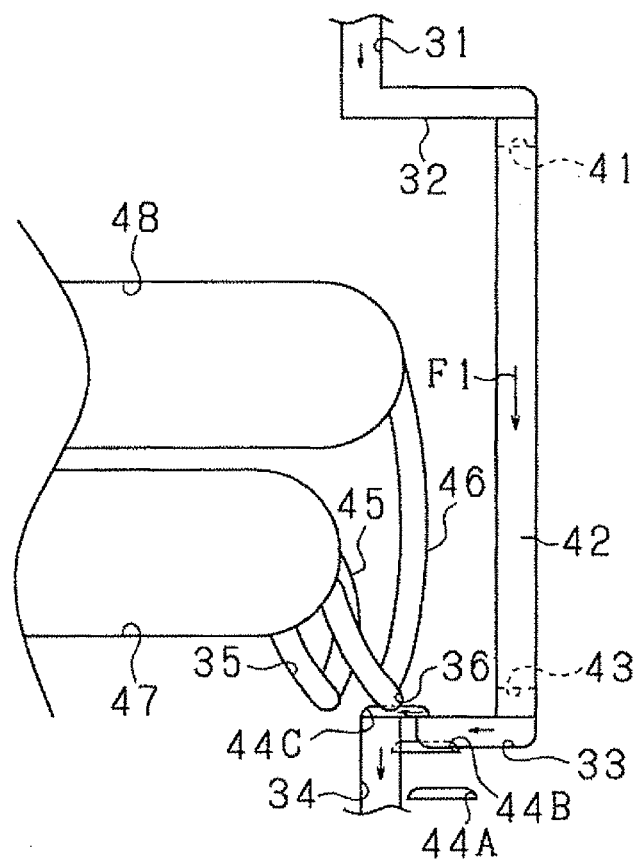
FIG. 14A is a pattern diagram illustrating the flow passage configuration of the injector during sample injection.
Figure 14B:
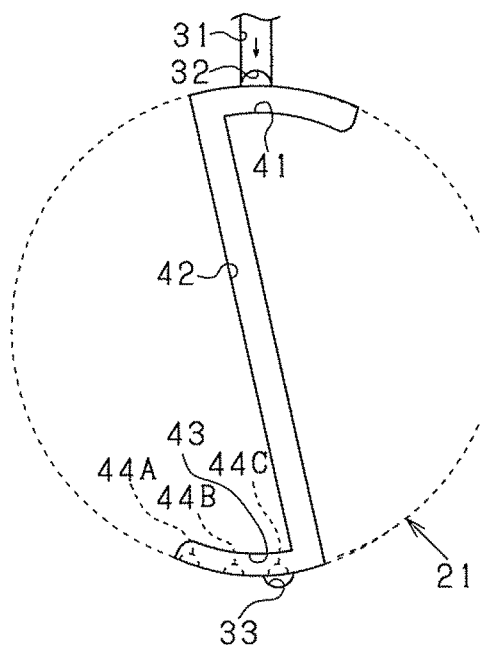
FIG. 14B is a pattern diagram illustrating the flow passage configuration of the injector during sample injection.

Next, the flow passage configuration of the injector 13 during injection of the sample solution S will be described using FIGS. 10 to 14B. Here, the flow series shown in FIGS. 7B to 7D will be described. FIGS. 10, 11 and 13 are perspective views illustrating the flow passage configuration of the injector 13 during sample injection, and correspond to FIG. 8 described above. FIGS. 12A, 12B, and 14 are pattern diagrams illustrating the flow passage configuration of the injector 13 during sample injection, and correspond to FIG. 9 described above.

To implement sample injection, first, the rotary body 21 is shifted from the state shown in FIG. 7A to the state shown in FIG. 7B. In this case, a state shown in FIG. 10 is established, whereby the flow of the mobile phase solvent M through the recess portion chamber 44A is halted and sample charging with respect to the recess portion chamber 44B is terminated.

The rotary body 21 is then rotated further to reach the state shown in FIG. 7C. In this case, a state shown in FIGS. 11, 12A, and 12B is established, whereby the sample solution S charged to the recess portion chamber 44B is injected into the mobile phase solvent M flowing through the solvent flow path and then discharged together with the mobile phase solvent M to the downstream side (the column side). At this time, the sample solution S is measured to a predetermined amount when charged into the recess portion chamber 44B, and therefore the sample charging amount can be specified accurately without performing a separate measurement.

In this embodiment, the outflow side passage 34 of the support member 23 is formed as an extremely narrow hole having a diameter of 25 µm. The reason for forming the outflow side passage 34 in this manner is to suppress intermixing of minute amounts of approximately several nanoliters of the sample solution S into the mobile phase solvent M during discharge of the sample solution S. However, processing difficulties occur when attempting to lengthen such a narrow hole 34, and therefore, by forming a recess portion 37, the length of the outflow side passage 34 can be shortened to a processable length L.

In this embodiment, the mobile phase solvent M continues to flow even after the sample solution S has been injected. Hence, during isocratic analysis, the sample solution S is discharged from the column 15 such that conditioning of the column 15 is completed in a short amount of time.

Further, when a first sample injection operation is complete, the rotary body 21 is rotated further to reach the state shown in FIG. 7D, whereupon a second sample injection operation is performed. In this case, a state shown in FIGS. 13, 14A, and 14B is established, whereby, similarly to the first sample injection operation, the sample solution S charged to the recess portion chamber 44C is injected into the mobile phase solvent M flowing through the solvent flow path and then discharged together with the mobile phase solvent M to the downstream side (the column side).

The recess portion chamber 44C may be constituted such that a larger amount of sample solution can be charged thereto than to the recess portion chamber 44B, for example. In so doing, different amounts of the sample solution S can be injected continuously within a short amount of time.

Hence, with the injector 13 according to this embodiment, two continuous analyses can be performed within a short amount of time during isocratic analysis, for example. Further, an increase in measurement freedom can be achieved easily with respect to the injection amount and number of continuous injections of the sample solution S.

Note that the analysis method does not necessarily have to be isocratic analysis. However, isocratic analysis is advantaged in that continuous measurements can be taken within a short period of time, and therefore isocratic analysis is used as the analysis method applied to this embodiment.

In the embodiment described above, the two recess portion chambers 44B, 44C are connected in series between the groove portions 35, 36, but the number of recess portion chambers may be one, three, or more. Further, all of the recess portion chambers 44 may have identical capacities (charging capacities), or a part of the recess portion chambers 44 may have identical capacities while the other recess portion chamber 44 has a different capacity.

D. Other Typical Configurations

Further, communication among the passages described above is realized by having the medium passage and sample passage of the first member (the rotary body 21) and the discharge passage of the second member (support members 23) open onto the outer peripheral surfaces of the respective members and making the first member and the second member capable of a relative sliding motion while the respective arc-shaped outer peripheral surfaces thereof maintain surface contact. By forming a contact surface of the second member in an arc shape to enable the relative sliding motion in this manner, leakage from the contact surface can be managed appropriately, and therefore flow passage switching and sample injection amount measurement can be realized without the use of at least one of a complicated bearing mechanism and an elastic sealing member, for example. Accordingly, the present invention can be used favorably in a chromatography apparatus that supplies the mobile phase medium in a high-pressure state, for example.

Furthermore, with the above constitution, in which the relative sliding motion can be performed while surface contact is maintained between the respective arc-shaped outer peripheral surfaces, a surface pressure distribution can be adjusted by differentiating a radius of a recessed arc-shaped outer peripheral surface (also referred to as a recessed arc-shaped surface) from a radius of a projecting arc-shaped outer peripheral surface (also referred to as a projecting arc-shaped surface), and thus a degree of design freedom can be provided. As a result, a sealing performance with respect to communication among the respective flow passages can be set freely in accordance with design specifications of the sample injector. More specifically, constitutions such as the following, for example, can be implemented.

By setting the radius of the recessed arc-shaped surface to be smaller than the radius of the projecting arc-shaped surface, surface pressure can be generated over a large region of the contact surface when the respective arc-shaped surfaces are pressed into close contact with each other. Thus, a region in which a sufficient sealing performance is secured relative to specifications can be realized without the use of an elastic sealing member, for example, and as a result, the design freedom (the number of sample chambers, for example) of the flow passages can be increased.

Conversely, by setting the radius of the recessed arc-shaped surface to be larger than the radius of the projecting arc-shaped surface, a surface pressure distribution having a sharp peak in a most recessed part of the recessed arc-shaped surface (also referred to as a linear region in an axial direction of an apex portion of the recessed portion) can be realized. The reason for this is that the respective arc-shaped surfaces are brought into close contact by large elastic deformation in the most recessed part of the recessed arc-shaped surface. This constitution is favorable in a case where a pressure in the flow passage for charging the sample is low such that sealing performance requirements are low, whereas a pressure in the flow passage for injecting the sample into the mobile phase medium in the sample injection position is extremely high such that a high sealing performance is required locally, for example. Alternatively, a precise fitting tolerance may be set.

Hence, in the above configuration, the relative sliding motion can be performed while surface contact is maintained between the respective arc-shaped outer peripheral surfaces, and therefore the sealing performance with respect to communication among the respective flow passages can be set freely in accordance with the design specifications of the sample injector.

A second aspect is the sample injector according to the above aspect, wherein the plurality of sample chambers are provided along a direction of the relative sliding motion of the first member and the second member.

According to the second aspect, the sample chamber is provided in a plurality extending in the relative movement direction of the first member and the second member, and therefore the sample injection position is set in a plurality of positions having different movement amounts in the relative movement direction. In this case, sample injection can be implemented from the plurality of sample chambers simply by moving the first member and the second member relative to each other.

A third aspect is the sample injector according to the second aspect, wherein the plurality of sample chambers include sample chambers having different capacities.

According to the third aspect, the plurality of sample chambers include sample chambers having different capacities, and therefore different volumes of the sample can be injected consecutively.

A fourth aspect is the sample injector according to any one of the first to third aspects, wherein a medium chamber is formed in a recessed shape in the outer peripheral surface of either one of the first member and the second member. The medium chamber is capable of being loaded with the mobile phase medium flows. At least one of the first member and the second member is configured to move to a medium outflow position. The medium chamber connects with the medium passage and the discharge passage in the medium outflow position, whereby the mobile phase medium in the medium passage flows out into the discharge passage via the medium chamber.

According to the fourth aspect, at least one of the first member and the second member is capable of moving to the medium outflow position in which the medium chamber formed in the outer peripheral surface of one of the first member and the second member connects with the medium passage and the discharge passage such that the mobile phase medium in the medium passage flows out into the discharge passage via the medium chamber. By providing the medium chamber in addition to the sample chamber, the mobile phase medium alone can be supplied continuously to a test container (a column or the like) on a downstream side of the sample injector using the medium chamber. As a result, the test container can be conditioned, or in other words the state of the mobile phase medium in the test container can be stabilized.

A fifth aspect is the sample injector according to the fourth aspect, wherein the sample chamber and the medium chamber are provided in series in a direction of the relative sliding motion of the first member and the second member. A groove portion is formed in the first member in an outer peripheral surface-side end portion of the medium passage, the groove portion extending in the direction of the relative sliding motion of the first member and the second member, the groove portion having at least an equal length to a separation distance between the sample chamber and the medium chamber.

According to the fifth aspect, the groove portion having at least an equal length to the separation distance between the sample chamber and the medium chamber and extending in the relative movement direction of the first member and the second member is formed in the outer peripheral surface-side end portion of the medium passage. As a result, communication between the medium passages in the first member and the second member can be maintained via the groove portion even when relative movement of the first member and the second member to the medium outflow position and the sample injection position occurs.

A sixth aspect is the sample injector according to any one of the first to fifth aspects, wherein a collecting passage is formed in the first member to connect with the sample chamber, the collecting passage being for collecting a surplus of the sample charged into the sample chamber.

According to the sixth aspect, sample charging to the sample chamber and collection of the surplus sample via the collecting passage can be performed simultaneously when the relative positions of the first member and the second member correspond to the sample charging position. As a result, when air bubbles or the like exist in the sample chamber, the air bubbles or the like can be removed so that charging can be performed reliably.

Note that the collecting passage is preferably formed to be communicative when the sample passage and the sample chamber are connected and non-communicative when the sample passage and the sample chamber are disconnected.

A seventh aspect is the sample injector according to any one of the first to sixth aspects, wherein the outer peripheral surface of the first member has a larger curvature radius than a curvature radius of the outer peripheral surface of the second member.

According to the seventh aspect, the outer peripheral surface of the first member has a smaller curvature radius than the outer peripheral surface of the second member, and therefore a peak of a surface pressure distribution on a contact surface between the first member and the second member is alleviated such that leakage can be suppressed over a large region. Moreover, leakage can be suppressed even when the relative positions of the first member and the second member are greatly varied, and therefore the relative movement amount between the first member and the second member can be increased.

An eighth aspect is the sample injector according to any one of the first to seventh aspects further comprises a third member configured to press and support the first member against the second member on an opposite side of the first member to the second member, wherein the first member is rotatably provided between the second member and the third member.

According to the eighth aspect, the first member can be pressed and supported from either side by the second member and the third member, and therefore the first member can be supported easily.

A ninth aspect is the sample injector according to the eighth aspect, wherein the first member is rotatably supported by the second member and the third member, the first member having an outer peripheral surface in a projecting arc shape contacting the second member and the third member, the second member and the third member having opposing outer peripheral surfaces in a recessed arc shape.

According to the ninth aspect, the outer peripheral surface of the first member can be formed as a part of a perfect circle, and therefore the first member can be manufactured easily using a lathe or the like.

E. Modified Examples

The present invention is not limited to the content described in the above embodiments and may be implemented as follows, for example.

Figure 15:
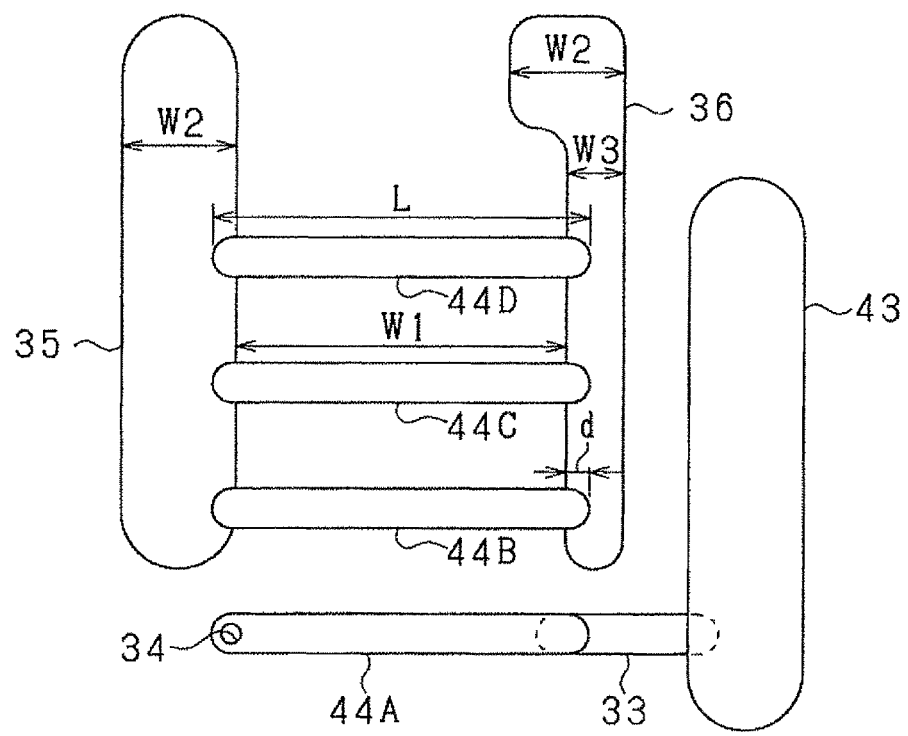
FIG. 15 is an enlarged sectional view showing a flow passage configuration of an injector during injection according to a modified example.

(a) In the above embodiment, the two groove portions 35, 36 are formed as grooves that extend in the circumferential direction at a uniform and identical width. However, as shown in FIG. 15, for example, the groove portions 35, 36 may be formed such that the widths thereof take an identical width W2 in positions linked to the sample outflow passage 45 and the sample inflow passage 46 and the width of the collecting recess portion 35 narrows to W3 in positions linked to the two recess portion chambers 44B, 44C.

In so doing, an interval between the groove portions 35, 36 can be enlarged, and as a result, the length L of the two recess portion chambers 44B, 44C can be increased, leading to an increase in loading capacity, without making a length of an intersection amount d excessive. To ensure that the sample solution S is charged reliably, the intersection amount d is preferably no more than twice the length of the groove-shaped recess portion in a width direction (a perpendicular direction to the direction of the length L), and more preferably no more than this width direction length.

Further, when loading amounts of the respective recess portion chambers 44B, 44C differ greatly from each other, an appropriate intersection amount d can be maintained by partially adjusting the width of the distribution recess portion 36 and the collecting recess portion 35.

(b) In the above embodiment, the recess portion chambers 44A, 44B, 44C are formed on the rotary body 21 side, but the recess portion chambers 44A, 44B, 44C may be formed on the support member 22 side, for example. In this constitution, the two groove portions 35, 36 and the groove portion 33 are formed on the rotary body 21 side while the groove portion 43 is formed on the support member 22 side.

However, the above embodiment is advantaged in that the measurement parameters can be modified easily simply by preparing a plurality of rotary bodies 21 having different numbers of recess portion chambers 44A, 44B, 44C and different loading capacities and exchanging the plurality of rotary bodies 21.

(c) In the above embodiment, the two groove portions 35, 36 are provided on one side of the groove portion 33 in the circumferential direction, but the two groove portions 35, 36 may be provided on both sides of the groove portion 33 in the circumferential direction. In so doing, the sample solution S can be loaded and injected during both outward and return operations of the rotation operation, while loading and injection can be repeated alternately. As a result, an improvement in operational efficiency can be achieved.

(d) In the above embodiment, the rotary body 21 serving as the first member is formed in a columnar shape, but the rotary body 21 does not have to be formed in a columnar shape, and as long as the contact surface of the rotary body 21 that contacts the support members 22, 23 is arc-shaped so that the rotary body 21 can rotate while supported by the support members 22, 23, the shape of the remaining parts thereof is arbitrary.

(e) In the above embodiment, a first member (the rotary body 21 according to the above embodiment) formed with a medium passage and a sample passage and a second member (the second support member 23 according to the above embodiment) provided in close contact with the first member and formed with a discharge passage are constituted such that the second member is fixed and the first member moves relative to the second member. However, this constitution may be modified such that the first member is fixed and the second member moves relative to the first member. Further, the first member and the second member may both be constituted to be capable of moving such that a relative movement amount thereof can be adjusted.

Furthermore, a contact surface on the first member side may be formed in a recessed shape while a contact surface on the second member side is formed in a projecting shape.

(f) A relative movement direction of the first member and the second member is not limited to a circumferential direction centering on a rotary axis, and may be an axial direction of the rotary axis. In this case, the relative movement direction of the two members is modified by 90° when the two members are seen deployed on a plane, and therefore the arrangement of the passages provided in the rotary body 21 and the respective support members 22, 23 is also modified by 90° (note, however, that in this case, rotation is not essential). Likewise with this constitution, flow passage switching can be realized in the injector 13 in a similar manner to that described above.

(g) In the above embodiment, the present invention is applied to a liquid chromatography apparatus using the mobile phase solvent M as a mobile phase medium. Alternatively, however, the present invention may be applied to a gas chromatography apparatus that uses a gas as the mobile phase medium.

Although the present invention has been described and illustrated in detail, it is clearly understood that the same is by way of illustration and example only and is not to be taken by way of limitation, the spirit and scope of the present invention being limited only by the terms of the appended claims.

The invention claimed is:

1. A sample injector for injecting a fixed amount of a sample into a mobile phase medium and discharging the mobile phase medium with the sample, the sample injector comprising:
    a first member having a first outer peripheral surface having a convex curve, the first member including a medium passage for supplying the mobile phase medium and a sample passage for supplying the sample, the medium passage and the sample passage having openings on the first outer peripheral surface;
    a second member having a second outer peripheral surface having a concave curve, the second member including a discharge passage for discharging the mobile phase medium with the sample to an outside of the injector, the discharge passage having an opening on the second outer peripheral surface, the second member being in contact with the first member; and
    a sample chamber having a recessed shape, formed on either one of the first and second outer peripheral surfaces, the sample chamber being configured to receive and hold a prescribed amount of the sample,
    wherein the first and second outer peripheral surfaces are in surface contact with each other so as to allow a relative sliding motion of the first member and the second member between a sample charging position and a sample injection position thereof,
    wherein the sample chamber connects to the sample passage when the first and second members are in the sample charging position such that the sample flowing through the sample passage is charged into the sample chamber,
    and wherein the sample chamber connects to the medium passage and the discharge passage when the first and second members are in the sample injection position such that whereby the sample held in the sample chamber is injected into the mobile phase medium flowing through the medium passage.

2. The sample injector according to claim 1, wherein a plurality of sample chambers are provided along a direction of the relative sliding motion of the first member and the second member.

3. The sample injector according to claim 2, wherein the plurality of sample chambers include sample chambers having different capacities.

4. The sample injector according to claim 1, further comprising:
    a medium chamber having a recessed shape, formed on either one of the first and second outer peripheral surfaces, the medium chamber being capable of receiving the mobile phase medium therein,
    wherein the first member and the second member are further capable of a relative sliding motion to a medium outflow position thereof, the medium chamber connecting to the medium passage and the discharge passage when the first and second members are in the medium outflow position, such that the mobile phase medium in the medium passage flows out into the discharge passage via the medium chamber.

5. The sample injector according to claim 2, further comprising:
    a medium chamber having a recessed shape, formed on either one of the first and second outer peripheral surfaces, the medium chamber being capable of receiving the mobile phase medium therein,
    wherein the first member and the second member are further capable of a relative sliding motion to a medium outflow position thereof, the medium chamber connecting to the medium passage and the discharge passage when the first and second members are in the medium outflow position, such that the mobile phase medium in the medium passage flows into the discharge passage via the medium chamber.

6. The sample injector according to claim 3, further comprising:
    a medium chamber having a recessed shape, formed on either one of the first and second outer peripheral surfaces the medium chamber being capable of receiving the mobile phase medium therein,
    wherein the first member and the second member are further capable of a relative sliding motion to a medium outflow position thereof, the medium chamber connecting to the medium passage and the discharge passage when the first and second members are in the medium outflow position, such that the mobile phase medium in the medium passage flows into the discharge passage via the medium chamber.

7. The sample injector according to claim 4, wherein the sample chamber and the medium chamber are provided in series in a direction of the relative sliding motion of the first member and the second member, the sample injector further comprising:
    a groove portion formed in the first member in an outer peripheral surface-side end portion of the medium passage, the groove portion extending in the direction of the relative sliding motion and having a length equal to or greater than a separation distance between the sample chamber and the medium chamber.

8. The sample injector according to claim 5, wherein the sample chamber and the medium chamber are provided in series in a direction of the relative sliding motion of the first member and the second member, the sample injector further comprising:
    a groove portion formed in the first member in an outer peripheral surface-side end portion of the medium passage, the groove portion extending in the direction of the relative sliding motion and having a length equal to or greater than a separation distance between the sample chamber and the medium chamber.

9. The sample injector according to claim 6, wherein the sample chamber and the medium chamber are provided in series in a direction of the relative sliding motion of the first member and the second member, the sample injector further comprising:
    a groove portion formed in the first member in an outer peripheral surface-side end portion of the medium passage, the groove portion extending in the direction of the relative sliding of the first member and the second member, the groove portion having a length equal to or greater than a separation distance between the sample chamber and the medium chamber.

10. The sample injector according to claim 1, further comprising:

a collecting passage is formed in the first member and connected to the sample chamber, a surplus of the sample charged into the sample chamber being collected via the collecting passage.

11. The sample injector according to claim 1, wherein the first outer peripheral surface of the first member has a curvature radius greater than a curvature radius of the second outer peripheral surface of the second member.

12. The sample injector according to claim 1, further comprising:
 a third member provided on an opposed side of the first member with respect to the second member, the third member pressing the first member against the second member such that the first member is rotatably supported between the second member and the third member.

13. The sample injector according to claim 12, wherein the third member has a third outer peripheral surface facing the second member with the first member interposed therebetween, the third outer peripheral surface having a concave curve, and the first outer peripheral surface being in sliding contact with the second outer peripheral surface and the third outer peripheral surface.

14. The sample injector according to claim 1, wherein the first outer peripheral surface of the first member has a curvature radius smaller than a curvature radius of the second outer peripheral surface of the second member.

15. The sample injector according to claim 1, wherein the first outer peripheral surface is substantially in a cylindrical shape.

* * * * *